US006820717B2

United States Patent
Fleming et al.

(10) Patent No.: US 6,820,717 B2
(45) Date of Patent: Nov. 23, 2004

(54) PRESSURE REGULATING EARPLUG

(75) Inventors: Thomas W. Fleming, San Diego, CA (US); Bill Nyugen, San Diego, CA (US); John A. Jenkins, Jr., San Marcos, CA (US)

(73) Assignee: Howard Leight Industries, LLC, San Diego, CA (US)

( * ) Notice: Subject to any disclaimer, the term of this patent is extended or adjusted under 35 U.S.C. 154(b) by 34 days.

(21) Appl. No.: 10/346,014

(22) Filed: Jan. 16, 2003

(65) Prior Publication Data

US 2004/0163882 A1 Aug. 26, 2004

(51) Int. Cl.[7] ................................................ A61B 7/02
(52) U.S. Cl. ...................... 181/135; 181/129; 181/130; 181/134; 181/128
(58) Field of Search .............................. 181/135, 129, 181/130, 134, 128

(56) References Cited

U.S. PATENT DOCUMENTS

| | | | | |
|---|---|---|---|---|
| 2,437,490 A | * | 3/1948 | Watson et al. | 128/867 |
| 2,487,038 A | * | 11/1949 | Jasper | 181/135 |
| 5,467,784 A | | 11/1995 | Mobley et al. | |
| 5,996,123 A | * | 12/1999 | Leight et al. | 2/209 |

* cited by examiner

Primary Examiner—Shih-Yung Hsieh
(74) Attorney, Agent, or Firm—Leon D. Rosen

(57) ABSTRACT

An earplug is provided for use by an airplane passenger, which more slowly increases the pressure of air in the passenger's ear canal than the rate of increase in cabin air pressure as the airplane descends near the end of a flight. The earplug has a cavity (30) that is open to the front end (20) of the earplug, and with a restrictor (24) at the front end of the cavity that allows air to pass between the cavity and ear canal, and the cavity to collapse, only at a very slow rate. As the environmental air pressure increases near the end of a flight, the earplug is slowly compressed in diameter and compresses the cavity.

13 Claims, 3 Drawing Sheets

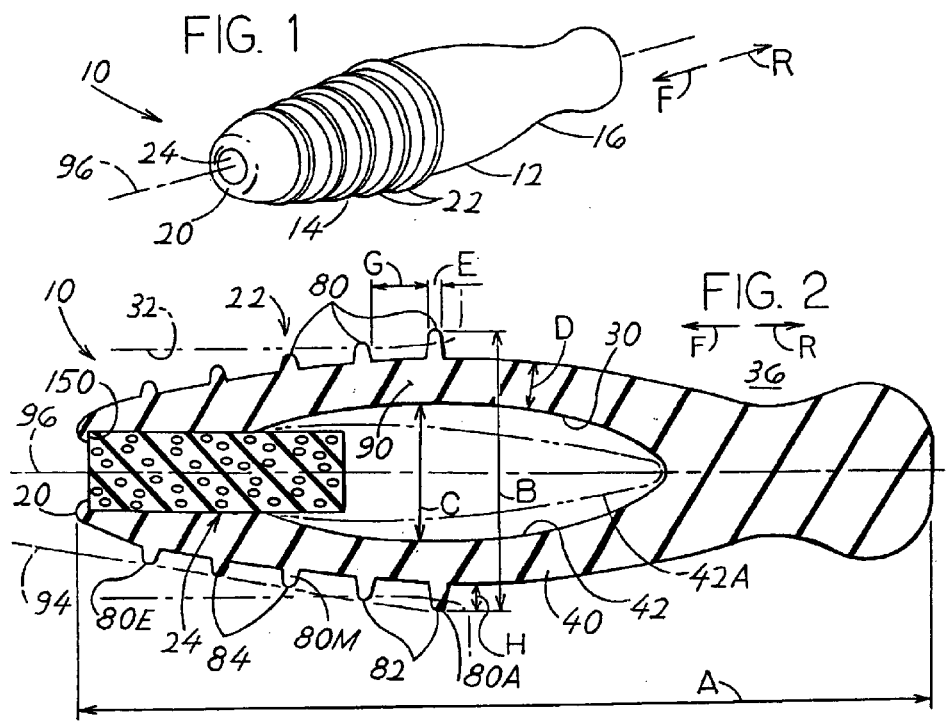
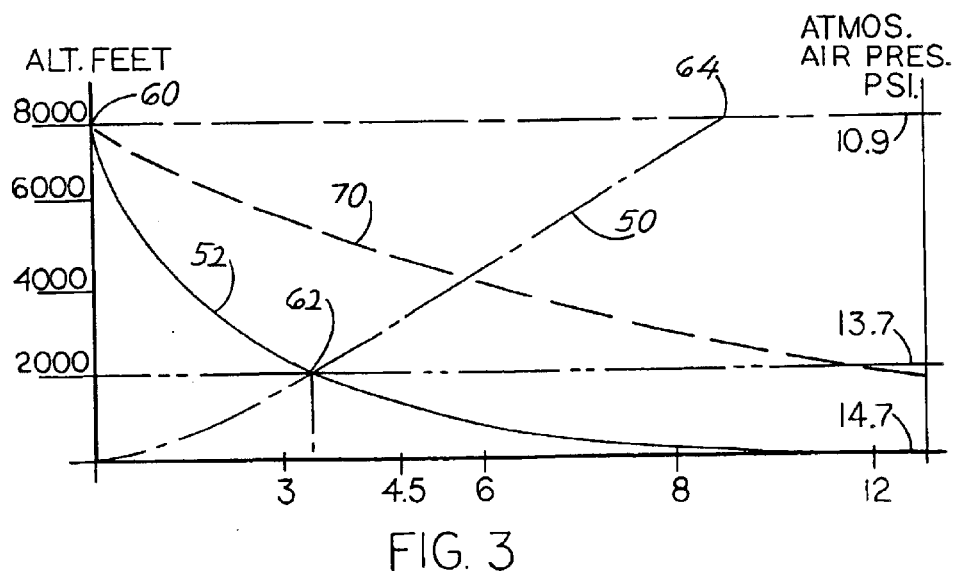

PRESSURE REGULATING EARPLUG

BACKGROUND OF THE INVENTION

Passenger airliners commonly cruise at a height of about 35,000 feet above sea level, but maintain a pressure that exists at about 8,000 feet above sea level when the airliner flies above 8,000 feet. As a result, a person's ears are subjected to pressure changes as the airliner ascends to about 8,000 feet and as the airliner descends from about 8,000 feet to sea level. In most people, their eustachian tube passes air between the environment and the inner ear so there is not a great pressure difference across the eardrum. However, in some people the eustachian tubes do not open sufficiently to allow air to be exchanged between the ambient environment and the middle ear. A result is a pressure differential across the eardrum and possible discomfort or pain. The discomfort or pain is experienced most acutely during airplane descent, when the cabin pressure increases from the pressure at about 8,000 feet above sea level to a pressure close to that at sea level. U.S. Pat. No. 5,467,784 describes an earplug with a bore extending between its opposite ends and with a pressure regulator lying along the bore, to very slowly pass air between the environment and the ear canal, so the rise in pressure in the ear canal is much slower than the rise in cabin pressure during a typical landing procedure. This provides time for air to leak through a person's eustachian tube if the eustachian tube is only slightly open. Other earplug constructions which delayed the change in ear canal pressure, especially during the descent part of the flight, would be of value.

SUMMARY OF THE INVENTION

In accordance with one embodiment of the present invention, a pressure regulating earplug is provided which delays the change in pressure in the ear canal as the cabin pressure changes, especially during the descent portion of a flight when the cabin pressure rapidly increases. The earplug is of the type that has an earplug body with a front portion for entering an ear canal and a rear portion for grasping to pull the earplug out of the ear canal, with the front portion having a front end and having a sealing portion of largest diameter that seals against the ear canal. The earplug body has a cavity that is open to the front end of the body, and the earplug includes an a restrictor that allows the passage of air between the cavity and ear canal but at a restricted flow rate. The restrictor can be formed from porous material that is preferably foam material, and preferably with a foam material that has been compressed, or felted. The restrictor can restrict the rate of air flow out of the earplug cavity to the ear canal, or restrict the rate at which the cavity collapses.

As the cabin air pressure increases during airplane descent, the walls of the earplug surrounding the cavity deflect inwardly and help to expel air in the cavity so the air slowly passes into the ear canal. The rate of increase in ear canal pressure depends on the elasticity of the earplug material, thickness of cavity walls, cavity design, and possibly on the sealing flanges on the outside of the earplug.

The novel features of the invention are set forth with particularity in the appended claims. The invention will be best understood from the following description when read in conjunction with the accompanying drawings.

BRIEF DESCRIPTION OF THE DRAWINGS

FIG. 1 is a front isometric view of an earplug constructed in accordance with one embodiment of the present invention.

FIG. 2 is a sectional view of the earplug of FIG. 1 in its initial state and showing, in phantom lines, the walls of the cavity compressed by a higher pressure in the environment than in the ear canal.

FIG. 3 includes graphs showing a general approximation of variation in cabin pressure with time, and variation in ear canal pressure with time when an earplug such as shown in FIG. 2 is used.

DESCRIPTION OF THE PREFERRED EMBODIMENTS

Figure 4:
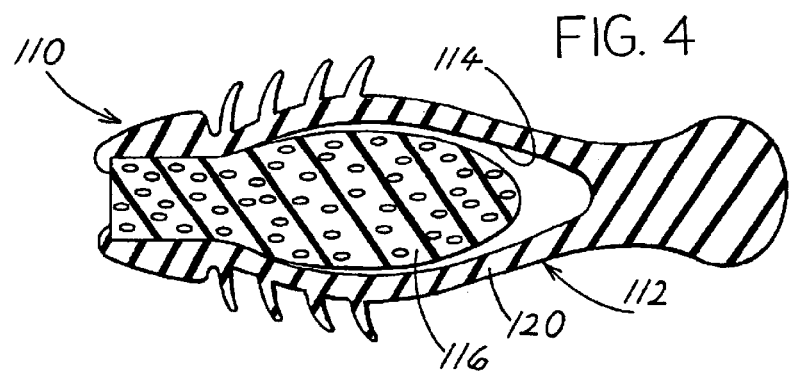
FIG. 4 is a sectional view of an earplug of another embodiment of the invention, wherein foam material fills most of the cavity.

FIG. 1 illustrates a pressure regulating earplug 10 of one embodiment of the invention, which includes an elastomeric an earplug body 12 having a front portion 14 for entering a person's ear canal and a rear portion 16 for grasping by a person to pull the earplug out of the ear canal. The front portion 14 has a front end 20, and has a sealing part 22 of largest diameter that seals against the ear canal. The body 12 has a large cavity that can be compressed, and has a restrictor, or restricted air-passing device 24 that allows the passage of air between the cavity and the person's ear canal, but only at a very slow rate.

FIG. 2 illustrates details of the pressure regulating earplug 10, showing the cavity 30 and the restricted air passing device 24. The cavity 30 is open only to the front end 20 of the earplug, through the air passing device 24, so air passes between the cavity 30 and the person's ear canal, indicated at 32, only through the air passing device 24. Assuming that the earplug 10 is installed in a person's ear canal, and the cabin pressure at 36 is increasing as an airplane descends below 8,000 feet, a pressure differential grows between the cabin pressure at 36 and the pressure in the ear canal 32. The inside of the cavity 30 is initially at the 8,000 feet pressure that also exists in the ear canal. As the cabin pressure at 36 increases, the walls 40 of the cavity behind the ear canal 32, begin to be collapsed by the higher cabin pressure at 36. As the cavity collapses, air in the cavity flows out through the restricted air passing device 24 into the ear canal to slowly raise the air pressure in the ear canal. However, the cavity 30 can be collapsed only very slowly, and therefore the pressure in the ear canal 32 rises only very slowly, because the device 24 allows air to pass out of the cavity at only a very slow rate. FIG. 2 shows the inside surface 42 of the cavity collapsed at 42A to about one-half of maximum collapse. As mentioned above, collapse occurs only slowly, despite the pressure differential between cabin pressure at 36 and pressure in the cavity 30, because air can escape from the cavity only very slowly through the device 24. When the earplug is later removed, it returns to its original shape.

FIG. 3 includes graphs which show, in a simplified manner, variation in cabin pressure as an airplane ascends and descends. The ambient pressure at sea level is about 14.7 psi (pounds per square inch). Although a modern jet airliner commonly cruises at about 35,000 feet, it lowers the air pressure only to about the pressure at 8,000 feet above sea level, which is about 10.9 psi. Graph line 50 indicates a possible change in airliner cabin pressure as an airliner ascends. The cabin pressure decreases at a moderate rate as the airliner ascends. This can be due to the airliner ascending at only a moderate rate due to the limited power of the engines. In FIG. 3, the airliner is shown ascending at a rate that requires about nine minutes to reach an altitude of 8,000 feet (or the pressure at 8,000 feet regardless of altitude), after which the air pressure is maintained constant. The graph 50 shows a delay of about five one-half minutes between the airliner reaching 2,000 feet and reaching 8,000 feet, during which the air pressure decreases by 2.8 psi.

Graph line 52 shows the cabin pressure increase as the airliner descends from an altitude of about 8,000 feet. In this example, there is a more rapid increase in cabin pressure as the airplane descends from 8,000 feet at point 60 to 2,000 feet at point 62, than during ascent from point 62 to point 64. In FIG. 3, the airplane is shown descending from 8,000 feet to 2,000 feet in about three and one-half minutes, instead of the five one-half minutes during ascent. Many people feel pain in their ears during the rapid increase in cabin pressure during descent. It also appears that air more readily flows out through the eustachian tube then in through it, which makes it more likely that a passenger will experience pain during decent than ascent. FIG. 3 also includes a graph line 70 representing change in air pressure in the ear canal 32 (FIG. 2) of a person wearing the earplug of FIG. 2, during decent of the airplane.

It can be seen from FIG. 3, that the change in air pressure in the person's ear canal along line 70, is much more gradual than along line 52, especially during descent from 8,000 feet to 2,000 feet. In FIG. 3, applicant shows a time period of twelve minutes for air pressure change along graph line 70, which is three and one-half times as long as the change along line 52. This much more gradual change in air pressure in the person's ear canal, provides time for air to leak through the person's eustachian tube into the inner ear, so there is a smaller pressure differential across the person's ear drum, resulting in reducing or eliminating discomfort or pain.

The sealing part 22 of the earplug of FIG. 2, which seals to the walls of the ear canal 32, includes a plurality of flanges 80 of varying outside diameters. When the earplug is inserted into a person with a larger diameter ear canal, only the rearmost flanges 82 will be sealed against the person's ear canal. When the earplug is inserted into a person with a smaller ear canal, additional flanges 84 that lie more forward will also be deflected and seal against the person's ear canal, and the earplug may not be inserted so far into the ear canal.

As the cabin pressure increases and the walls 40 of the cavity are compressed, air in the cavity 42 is slowly expelled through the device 24 into the person's ear canal to very slowly increase air pressure in the ear canal. During such cavity compression, the wall portion 90 of the cavity where the flanges 80 are located, is also reduced in diameter. This may allow a very slow flow of air around the flanges into the person's ear canal, in a self-regulating manner.

Tests made on the earplug illustrated in applicant's FIG. 2, show that the earplug is effective in slowly reducing the difference in air pressure between the cabin and ear canal as the pressure increases during airplane descent. The exact mechanism by which this occurs is not fully understood.

The restricted air passing device 24 is formed of a felted foam. Applicant places a foamable material in a mold cavity and allows it to expand as it foams. The foam is compressed during foaming, as by providing a cavity of only small volume for a given amount of foamable material. Alternatively, the foamed material can be compressed soon after foaming. The compression of the foam, or felting, results in a resilient foam, but one which is much stiffer than foam that has not been felted, and with smaller pores. Applicant prefers to use a slow recovery foam material such as a slow recovery PVC. Although the density of felted foam is greater than unfelted foam, they both have a density less than 1.0 and will not fall out when the earplug is shaken. They both have open cells that hold air, and most of the volume is filled with air when uncompressed.

In an earplug 10 of the construction illustrated in FIG. 2 that applicant has made and successfully tested, the overall length A was 1.308 inch and the maximum diameter B was 0.460 inch. The easily compressed walls of the cavity had an average thickness D of about 0.08 inch. The initial maximum diameter C of the cavity 30 was 0.22 inch and its length (up to the front end of device 24) was about 0.8 inch. The initial cavity volume (including the volume of device 24) was about 600 mm$^3$, which was about 25% of the total volume of the earplug. The volume of the cavity not occupied by the device 24 was 200 mm$^3$ or 12% of total earplug volume. A cavity volume that is at least 8% of the entire earplug volume (or at least 190 mm$^3$) is preferred, in order to have a significant effect.

Each sealing flange 80 had a thickness E of 0.024 inch, and the flanges were spaced apart by a distance G at 0.085 inch. The flanges lay on an incline 94 of 10° from the axis 96 of the earplug. The largest diameter flange 80A had a height H of 0.05 inch while the smallest diameter flange 80E had a height of 0.024 inch. At least half the length of the compressible portion of the cavity 30 lay behind a middle sealing portion at flange 80M. Applicant believes that this construction may aid in compressing the cavity and possibly allowing cabin air to leak around the earplug. This earplug produced a very gradual reduction in ear canal pressure (in a special machine that simulates in-flight conditions).

FIG. 4 illustrates an earplug 110 of another embodiment of the invention, wherein the earplug body 112 has a cavity 114, with most of the volume of the cavity occupied by a mass 116 of elastomeric foam material (which consists primarily of air) which forms a restrictor. The foam mass 116 resists compression of the walls 120 of the cavity 116 to slow the outflow of air contained in the foam mass while also moderately restricting the outflow of air from around the foam.

Figure 5:
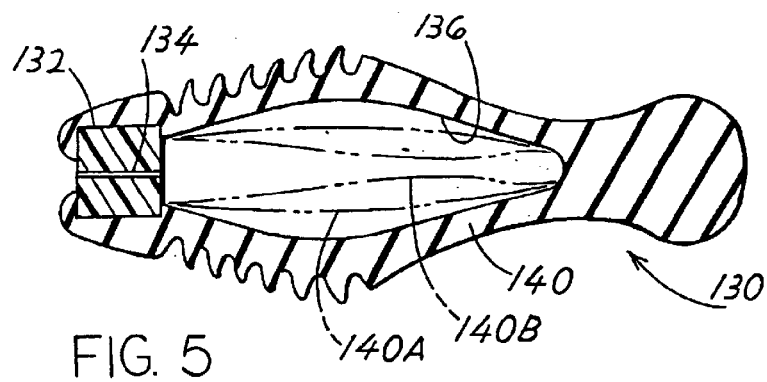
FIG. 5 is sectional view of an earplug of another embodiment of the invention, wherein a flow restrictor device is used.

FIG. 5 illustrates another earplug 130 wherein a restricted air passing device, or restrictor 132 is formed by a rigid plastic (specific gravity not much more than 1.0) cylinder with a very narrow passage 134. Compression of the cavity 136 is determined by the elasticity of the earplug material, the thickness of the cavity walls, and the shape of the sealing flanges on the outside of the earplug, as well as the restrictor 132. FIG. 5 shows the cavity walls 140 partially compressed at 140A and almost completely compressed at 140B.

The restricted air passing devices shown in the figures are held in place largely by an undercut such as 150 in FIG. 2. In addition, the devices can be fixed in place by bonding to the inside walls of the front end of the cavity. Applicant prefers to use restricted air-passing devices which flow air therethrough at a rate on the order of magnitude of 35 to 70 cubic millimeters per minute at a pressure differential of 1 psi.

Figure 6:
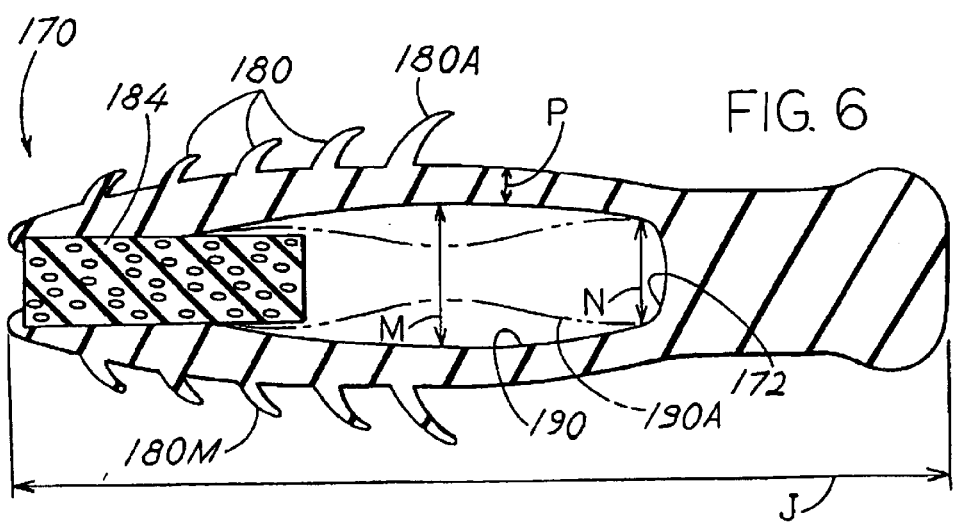
FIG. 6 is a sectional view of an earplug of another embodiment of the invention.

FIG. 6 shows an earplug 170 that is similar to the earplug 10 of FIGS. 1 and 2, but with some modifications. The length J of the earplug is the same as the length A. The cavity has a maximum diameter M of 0.20 inch, which decreases to a diameter N of 0.14 inch at the cavity rear end 72. This provides an increased cavity volume. The cavity wall thickness P is 0.055 inch from the rearmost flange 180A to substantially the rear of the cavity at 172. This results in a ratio of wall thickness P to average cavity width behind the rear flange 180A of 3.2. As a result, the rear portion 182 of the earplug, behind flange 180A is more easily compressed. A restrictor 184 of felted foam restricts the flow of air out of the cavity.

The flanges 180 have a greater radial extension than the flanges of FIG. 2, and have tapered thicknesses. This provides a more reliable initial seal. However, when the cavity collapses, as from 190 to 190A, most of the reduction in diameter occurs within the flange 180A and it is possible that the seal may slowly leak air.

Figure 7:
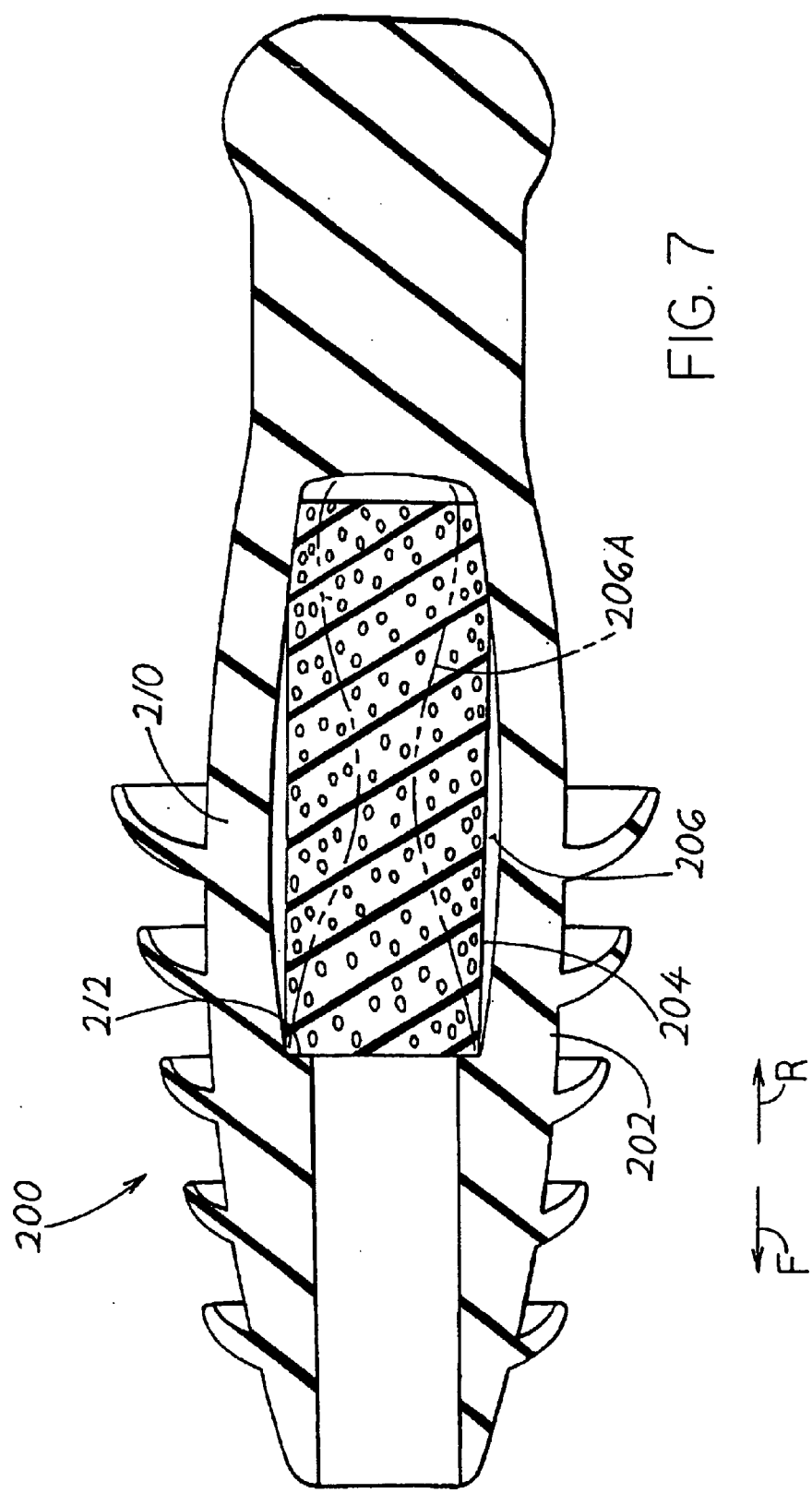
FIG. 7 is a sectional view of an earplug of another embodiment, which applicant has found to be the most effective to date.

FIG. 7 illustrates another earplug 200 that is similar to the earplug of FIG. 6, but with modifications. The earplug 200 includes a body 202 of elastomeric material and a restrictor 204 lying in a cavity 206 at the middle of the body. The restrictor is formed by a quantity of elastomeric resilient felted foam that is filled with air (when not compressed), and that fills about 80% of the volume of the cavity. The restrictor 204 resists rapid compression of walls 210 of the cavity, as to the compressed state 206A. With a pressure difference of 1 psi between the ear canal and cabin pressure, it requires over one minute to reduce the cavity volume by one-fourth.

When handling the earplug 170 of FIG. 6, applicant found that the restrictor 184 could be inadvertently pushed rearwardly until it lay entirely in the cavity. In the earplug 200 of FIG. 7, the front end of the cavity is formed with a rearwardly-facing shoulder 212 that holds the restrictor in the cavity. The restrictor then allows only slow compression of the cavity. Otherwise, the earplug 200 is of the same dimensions as the earplug 170 of FIG. 6, although the restrictor is somewhat larger.

It is noted that during airplane ascent, when the cabin pressure decreases, some people feel discomfort until their eustachian tubes open. An ordinary earplug can be placed in the ear before ascent to avoid such discomfort, and later removed during flight. The present pressure regulating earplug can be used for this purpose. The present earplug is particularly useful during airplane descent.

Thus, the invention provides a pressure regulating earplug which is especially useful for airline passengers, although there are other instances when it can useful, such as on aerial trams that ascend to great heights. The earplug has a cavity open at its front end to the person's ear canal. The earplug also includes a restrictor that restricts the flow of air through the cavity front end between the cavity and the person's ear canal. The restrictor can act only to restrict the flow of air as the cavity collapses, or can act to restrict the collapse of the cavity in the earplug body and thereby restrict the outflow of air. The earplug is constructed so the walls of the cavity compress when the cabin pressure increases and the ear canal pressure does not increase as fast. When the walls of the cavity compress sufficiently, it may be possible for air to leak around the outside portion of the earplug that otherwise seals to the walls of the ear canal.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A pressure regulating earplug which includes an elastomeric earplug body with a front portion for entering an ear canal and a rear portion for grasping by a person to pull the earplug out of the ear canal, said front portion having a front end and having a sealing part lying rearward of said front end and constructed to seal to the walls of the ear canal wherein:

said earplug body has a cavity open only to said front end, said cavity being at least partially collapsible when air pressure around part of the cavity increases, and including a restrictor that allows but restricts the rate of flow of air from the cavity to the ear canal through said front end.

2. The earplug described in claim 1 wherein:

said restrictor lies in said cavity and supports the walls of said cavity at least when the cavity is partially collapsed, to allow only a slow further collapse of the cavity.

3. The earplug described in claim 1 wherein:

said cavity has a front end and said restrictor lies in said cavity front end to slow the rate of air flow out of said cavity and into the ear canal.

4. The earplug described in claim 1 wherein:

said restrictor comprises a quantity of foam.

5. The earplug described in claim 4 wherein:

said quantity of foam comprises felted foam.

6. The earplug described in claim 1 wherein:

said cavity, without said restrictor, has a volume of at least 190 mm$^3$.

7. The earplug described in claim 1 wherein:

said cavity is constructed to collapse by at least one-fourth its original volume when the air pressure outside said cavity is at least 1 psi greater than the air pressure in said cavity.

8. The earplug described in claim 1 wherein:

said restrictor is constructed to slow the rate of flow of air into the ear canal to a rate on the order of magnitude of 35 cubic millimeters per minute at a pressure differential of 1 psi.

9. The earplug described in claim 1 wherein:

said earplug is partially inserted into the ear canal;

said cavity has cavity walls that lie rearward of the ear canal, so at least a rear portion of said cavity can be readily compressed to less than three fourths its original diameter by a pressure difference of more than 1 psi.

10. The earplug described in claim 1 wherein:

said cavity occupies at least about 25% of the volume of said body.

11. A pressure regulating earplug which includes an elastomeric earplug body with a front portion for entering an ear canal and a rear portion for grasping by a person to pull the earplug out of the ear canal, said front portion having a front end and having a sealing part lying rearward of said front end and constructed to seal to the walls of the ear canal wherein:

said earplug body has a cavity open only to said front end, said cavity being at least partially collapsible when air pressure around part of the cavity increases, and including a restrictor that allows but restricts the rate of flow of air from the cavity to the ear canal through said front end;

said restrictor lies in said cavity and supports the walls of said cavity at least when the cavity is partially collapsed, to allow only a slow further collapse of the cavity.

12. A pressure regulating earplug which includes an earplug body having a front portion for entering an ear canal and a rear portion for grasping by a person to pull the earplug out of the ear canal, said front portion having a front end and having a sealing portion constructed to seal to the walls of the ear canal, wherein:

said earplug body has cavity walls forming a cavity with a front portion open to the ear canal and a rear end that is closed to prevent any passage of air therethrough, said cavity being compressible so the walls of the cavity are compressed when the air pressure outside the ear canal is higher than the air pressure inside the ear canal;

a restrictor lying at a front end of said cavity and resisting rapid collapse of the cavity so the cavity can be compressed only slowly.

13. The earplug described in claim 12 wherein:

said cavity collapses from an initial position to three-quarters of its volume at the initial position, when the difference in air pressure in the ear canal and outside the ear is one psi.

\* \* \* \* \*